United States Patent [19]

Calabrese

[11] Patent Number: 5,061,631
[45] Date of Patent: Oct. 29, 1991

[54] METHOD, APPARATUS AND SOLUTION FOR CALIBRATION OF PARTIAL PRESSURE VALUE

[75] Inventor: Gary S. Calabrese, North Andover, Mass.

[73] Assignee: Fisher Scientific Company, Pittsburgh, Pa.

[21] Appl. No.: 257,553

[22] Filed: Oct. 14, 1988

[51] Int. Cl.⁵ .................... G01N 31/00; G01N 21/00; G01N 7/00
[52] U.S. Cl. ...................... 436/11; 436/68; 422/68.1; 422/81; 73/1 R
[58] Field of Search ............ 422/68.1, 81, 82.01; 436/11, 16, 68, 50; 252/608.1; 73/1 R

[56] References Cited

U.S. PATENT DOCUMENTS

| | | | |
|---|---|---|---|
| 3,874,850 | 4/1975 | Sorensen et al. | 436/50 |
| 4,039,933 | 8/1977 | Moran | 324/29 |
| 4,116,336 | 9/1978 | Sorensen et al. | 206/524.8 |
| 4,151,108 | 4/1979 | Sorensen et al. | 436/11 |
| 4,163,734 | 8/1979 | Sorensen et al. | 436/11 |
| 4,361,539 | 11/1982 | Weinberg et al. | 422/68 |
| 4,361,540 | 11/1982 | Weinberg et al. | 422/68 |
| 4,424,276 | 1/1984 | Clark et al. | 436/50 |
| 4,443,407 | 4/1984 | Weinberg et al. | 422/68 |
| 4,567,748 | 2/1986 | Klass et al. | 436/11 |
| 4,722,904 | 2/1988 | Feil | 436/11 |

FOREIGN PATENT DOCUMENTS 0218469 4/1987 European Pat. Off. .
61-22246 1/1986 Japan .
1159629 7/1969 United Kingdom .

OTHER PUBLICATIONS

L. Vincze & S. Papp, "Individual Quantum Yields of . . . ." J. of Photochemistry, vol. 36 (1987) pp. 289-296.
Hugh A. Taylor, "Analytical Methods and Techniques for Actinometry" *Analytical Photochemical Analysis*(1971) 91-115.
C. G. Hatchard & C. A. Parker, "A New Sensitive Actinometer", Proc. Royal Soc. (London), vol. A235, pp. 518-536 (1956) (esp. 530).
C. A. Parker, "Induced Autoxidation of Oxalate for Reference to the Photolysis of Potassium Ferrioxalate," Trans. Faraday Soc., vol. 50, pp. 1213-1221 (1954).

*Primary Examiner*—David L. Lacey
*Assistant Examiner*—William K. Y. Chan
*Attorney, Agent, or Firm*—Alan M. Doernberg

[57] ABSTRACT

Electrodes for the measurement of pCO2 and/or pO2 are calibrated with an exposed aliquot of a calibration liquid. A constituent such as a ferrioxalate salt in the calibration liquid is converted to the gas in a reproducible concentration by exposure of the aliquot to light. In some instances, the calibration liquid is equilibrated with air prior to exposure. Some mechanisms of light generation of carbon dioxide also consume oxygen, so as to depress the pO2 value by a reproducible amount. The use of two different calibration liquids enables both one-point and two-point calibration of the Clark oxygen electrode and the Severinghaus pCO2 electrode of a blood gas instrument.

21 Claims, 4 Drawing Sheets

METHOD, APPARATUS AND SOLUTION FOR CALIBRATION OF PARTIAL PRESSURE VALUE

The present invention relates to methods and apparatus for measuring the partial pressure of a volatile component in a sample liquid such as the measurement of the partial pressure of carbon dioxide or of oxygen in an aqueous sample liquid (e.g., blood). The present invention includes means in such methods and apparatus to calibrate the measurement of such partial pressure and includes a solution composition used in such means.

Partial pressures of normally volatile components in liquids are frequently measured. For example, partial pressures of oxygen, of carbon dioxide or of both are measured in fermentation, in environmental analysis, in clinical diagnosis and in a variety of other contexts. One of the most developed contexts for such analyses is in the measurement of pH along with the partial pressures of oxygen and of carbon dioxide in arterial or venous blood (a field generally referred to as blood gas analysis). The enumeration of these three parameters is not meant, however, to limit the field to contexts where all three measurements are made concurrently, nor to exclude the simultaneous measurement of other parameters such as certain electrolytes (e.g., sodium, potassium, chloride, calcium or a combination of several or all of these) or certain sugars and other chemicals (e.g., glucose). The field rather includes any application where the partial pressure of a component such as carbon dioxide or oxygen is measured in a sample liquid.

While the instruments for making such measurements are of many designs, a prototypical instrument is the Instrumentation Laboratory 1312 blood gas instrument sold by the present assignee Fisher Scientific Company. The sensing portion of such instruments is described in U.S. Pat. Nos. 4,361,539 and 4,361,540, each issued Nov. 30, 1982, and 4,443,407, issued Apr. 17, 1984, each of Weinberg and Cormier and currently assigned to Fisher Scientific Company. Such instrument has a series of sensing electrodes in series: a Clark oxygen electrode, a Severinghaus carbon dioxide electrode, a pH sensing electrode and a reference electrode (for the carbon dioxide electrode and for the pH electrode). Note especially column 6 of U.S. Pat. No. 4,361,540 for a discussion of the structure and operation of this instrument in the sensing mode.

Such instrument may be calibrated with one or more calibrants of known pH, pCO2 and pO2 values prior to each sensing measurement, and may be calibrated with two calibrants upon start-up and periodically thereafter (or when the measurement of quality control liquids indicates that the instrument is out of calibration). Such one-point calibration after each sensing measurement is described in U.S. Pat. No. 4,039,933 to Moran (Aug. 2, 1977).

In performing such calibration, it is conventional to use liquid buffers for the pH measurement and humidified gases for the pCO2 and pO2 measurements. For example, as described at col. 8, lines 22-35 of U.S. Pat. No. 4,361,539, calibration gas can be bubbled through a bubble chamber and then the liquid flowed past the ports having the pCO2 and pO2 electrodes. Using the circuitry of U.S. Pat. No. 4,039,933, the voltage registered at the pCO2 electrode and the amperage measured at the Clark oxygen electrode can be used to generate a compensatory voltage in the circuitry of U.S. Pat. No. 4,039,933. In such circuitry, a stored reference value is compared to the value measured on the calibrator, and the difference therebetween is applied as an adjustment to the value calculated from the voltage measurement made at the electrode when the sample is present. For convenience, such adjustment will be considered as an instance of comparing the voltage measured on the calibrator to the voltage measured on the sample even though, technically, the comparison has actually been at the digital level between the reference value and the output of analog-to-digital conversion of the voltage measured on the calibrator.

The use of such gas mixtures in the calibration of blood gas instruments has led to the requirement that bulky gas tanks be present in close proximity to the blood gas instrument. Such tanks are often cumbersome in locations where blood gas measurements are made: in cardiac care, respiratory care and operating room areas of hospitals; and in some environments, such gas mixtures are unavailable. The elimination of such tanks would facilitate moving the blood gas instrument closer to where the blood is drawn.

The use of calibration liquids, including fluorocarbon emulsions, having defined values of pH, pCO2 and pO2, have been proposed in a number of patents, including U.S. Pat. Nos. 4,722,904 to Feil (1988) and 4,151,108 and 4,163,734 to Sorenson (1979), but such compositions have been used commercially only as quality control materials, and not for calibration of the instrument. See also Hitachi's Kokai 61/22246 (Jan. 30, 1986).

BRIEF DESCRIPTION OF THE INVENTION

Applicant's invention provides for the generation of a calibrant liquid of highly reproducible partial pressure of a normally-gaseous component (e.g., carbon dioxide) by photochemical means. The precursor or precursors of the normally-gaseous component (such as ferrioxalate complex ion) is present in a precise concentration in a liquid. After exposure of the liquid to light of appropriate wavelength, intensity and duration to generate the normally-gaseous component, the liquid is introduced into the measuring chamber for the partial pressure of that component. The measurement taken on such exposed liquid is taken as the calibration value for that electrode.

Accordingly, the present invention provides a method for the measurement of the partial pressure of a gas in a liquid sample which comprises the steps:

a) providing a calibration liquid having a defined concentration of a dissolved precursor of a gas, the liquid having a composition such that, upon exposure to light, the dissolved precursor reacts to form the gas;

b) exposing an aliquot of the calibration liquid to light of sufficient wavelength, intensity and duration to convert the precursor substantially completely to the gas;

c) conveying the exposed aliquot with the converted precursor to a measuring chamber for contact with a measuring element (e.g., electrode) for the partial pressure of the gas;

d) making a measurement with the measuring element on the exposed aliquot with the converted precursor;

e) conveying the exposed aliquot with the converted presursor away from the measuring element and conveying a liquid sample having an analyte value of the partial pressure of the gas into the measuring chamber in contact with the measuring element;

f) making a measurement with the measuring element on the liquid sample; and g) comparing the measurement made with the measuring element on the liquid sample to the measurement made with the measuring element on the exposed aliquot of calibration liquid.

The present invention further provides an apparatus for measuring the partial pressure of a gas in a liquid sample which comprises:

a) exposure means for exposing an aliquot of a calibration liquid to light;

b) a measuring chamber;

c) first conveying means for conveying an exposed aliquot of calibration liquid from the exposure means to the measuring chamber;

d) a measuring element (e.g., electrode) in operative contact with the measuring chamber;

e) second conveying means for conveying a liquid sample into the measuring chamber; and f) comparator means for comparing the measurement made by the measuring element on the liquid sample with the measurement made by the measuring element on the exposed aliquot of calibration liquid.

The present invention also provides an aqueous solution having a pH of 0 to 5 and comprising at least 0.3 millimoles per liter of oxalate, 0.1 to 200 millimoles per liter of iron (III); provided that if the oxalate concentration is greater than 15 millimoles per liter, then the iron concentration is not more than 5 millimoles per liter. The molar ratio of iron (III) to oxalate in such composition is preferably 100:1 to 1:7200, with more preferred ranges producing oxygen depletion or not as described below.

DETAILED DESCRIPTION OF THE INVENTION

Figure 1:
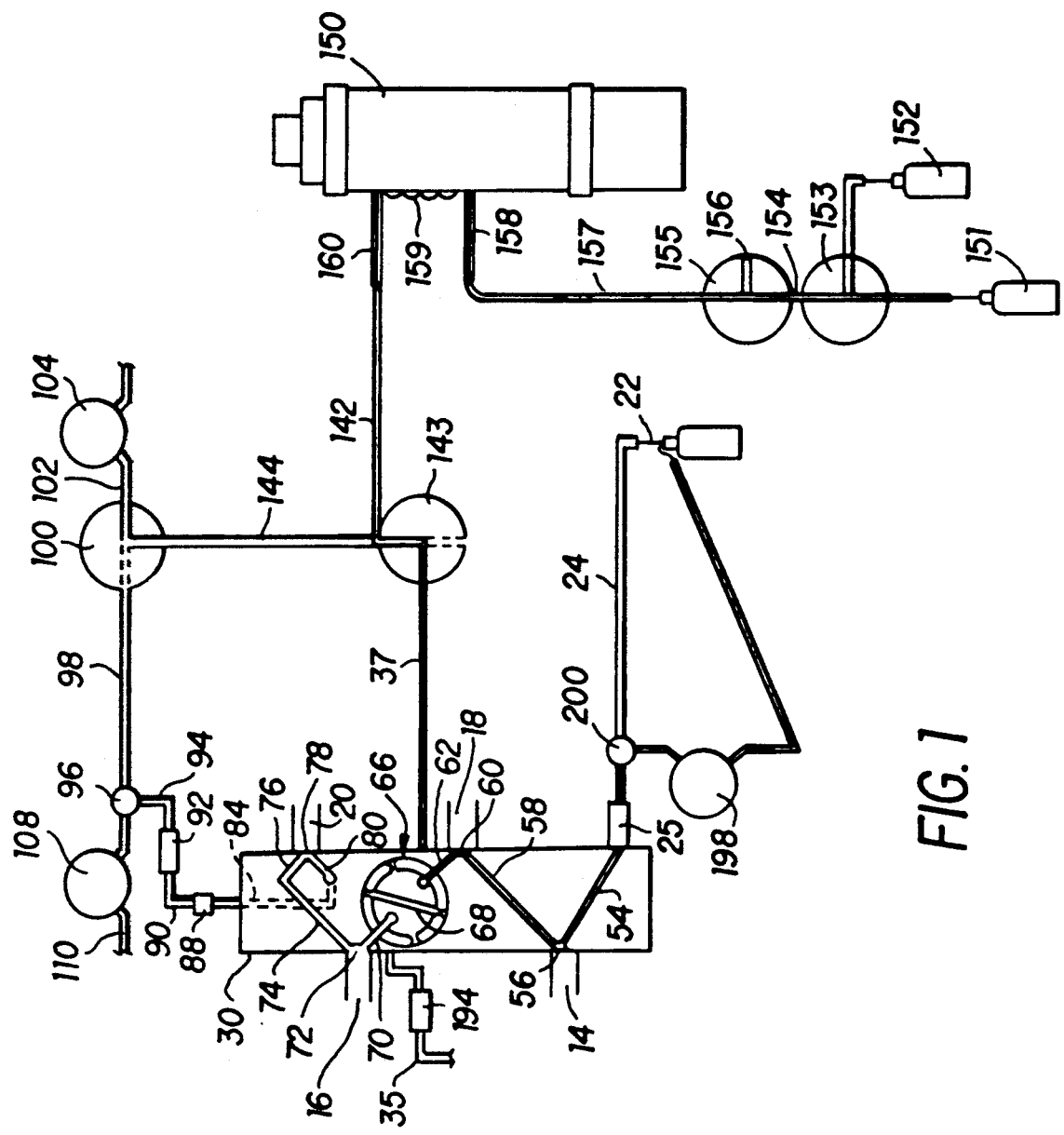
FIG. 1 is a schematic view of an apparatus according to a first embodiment of the present invention showing the overall relationship between the calibrator liquid storage vessel, the exposure device and the electrode assembly.

The calibration liquids of the present invention contain a precursor of the gas carbon dioxide or of the gas oxygen in a defined amount. The composition and amount (concentration) of such precursor is designed to yield, upon essentially complete photochemical conversion to the gas, a partial pressure of the gas in a range useful for calibration an instrument to measure that gas. Such precursor concentration is, in general, lower than would be the concentration of the same precursor in a liquid used to quantify the intensity of a light source. Nevertheless, many of the same precursor materials are also useful in the present invention, if they produce carbon dioxide or oxygen upon light exposure. In the case of oxygen, precursors are useful which either produce oxygen or consume oxygen, provided again that a partial pressure of oxygen in a useful range for calibration of instrument for measuring oxygen partial pressure results from the substantially complete photochemical conversion of the precursor. This principal is described in detail below for ferrioxalate as the precursor, but its application to other precursors will be readily understood.

A preferred class of precursors to carbon dioxide are the metal complexes of carboxylic acids, and especially such compex anions of oxalate such as ferrioxalate and uranyloxalate. Ferrioxalate, in its unexcited form, can be represented by the formula:

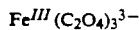

$$Fe^{III}(C_2O_4)_3{}^{3-}$$

and can be formed by mixing oxalate salts (typically the sodium or potassium salt) with iron (III) salts such as ferric chloride or ferric ammonium sulfate. Depending upon the pH, the ratio of Fe(III) to oxalate and their absolute concentrations, a number of species having, for each iron(III), one, two or three oxalates (and a charge of +1, −1 or −3, respectively) are believed to exist and to yield carbon dioxide upon exposure to light.

For reasons discussed below, the preferred total concentration of ferrioxalate in the calibration liquid for use with a blood gas instrument is about 0.25 to 5 millimoles per liter, especially about 0.5 to 2 millimoles per liter. Concentrations in that narrow range or higher, such as up to 5 millimoles per liter, may be used for calibrating other instruments that measure pCO2.

Other constituents of the calibration liquid are preferably adjusted in order to facilitate the conversion of the precursor to the gas (e.g., ferrioxalate to carbon dioxide) when intentionally exposed to light for that purpose, but to minimize any other decomposition of the precursor (especially thermally). In the case of ferrioxalate, it is therefore preferred that the calibration liquid be aqueous and have an acidic pH in the range of about 0 to about 5 (preferably about 0 to about 3, especially about 0 to about 2). If the pH of the aqueous solution is too high, the rate of thermal decomposition of the ferrioxalate may be unacceptably high. If the pH of the aqueous solution is too low, a proportion of the oxalate anions may be protonated and, in that form, too difficult to photooxidize.

In the case of ferrioxalate precursor liquids, the mechanism of photochemical decomposition permits two types of overall compositions: one in which the main follow-up reaction to the primary photoreaction is the reduction of iron from valence three to valence two, and another in which a the reduction of oxygen occurs. These two types of compositions can be appreciated by realizing that ferrioxalate complex ions are normally formed by separate introduction of oxalate anions and iron (III) cations into the solution. Molar ratios of iron-(III) to oxalate can be chosen such that one ingredient or the other will be the limiting reagent. Thus, if high iron(III) to oxalate ratios (e.g., 5:1 to 100:1, especially 10:1 to 50:1) are used, oxalate will be the limiting reagent, and the solution will contain hexaaqua iron (III) cations in a pH-dependant equilibrium with various iron(III) hydrolysis products in addition to the ferrioxalate complex anions.

There are various theories about which complexes of iron(III) and oxalate are converted by light to an initial, unstable reaction intermediate. Nevertheless, if iron(III) is present in excess, then the next reaction would be expected to be between that intermediate and another iron (III) species, to produce carbon dioxide and iron-(II). The experimental data supports the premise that such a mechanism that does not deplete oxygen is the primary mechanism for solutions having a stoichiometric excess of iron(III) over oxalate.

When iron(III) is present in near stoichiometric amounts or less, then the next reaction could also be between that intermediate and oxygen (dioxygen), if present, to form carbon dioxide and a reduced form of oxygen. The experimental data supports the premise that reaction of the intermediate with oxygen occurs to a sufficient extent such that oxygen is depleted; and the significant occurrence of such a reaction is the primary mechanism for solutions having a near stoichiometric amount or excess of oxalate over iron(III) (e.g., those with a molar ratio of iron(III) to oxalate of about 2:1 to 1:7200, especially about 1:1 to 1:2000).

In calibration solutions which are not used for calibrating oxygen electrodes (and thus for which the oxygen partial pressure after light exposure is not significant), either iron (III) or oxalate can be in stoichiometric excess or they can be at or near the 1:3 stoichiometric proportion.

Based upon the above reasoning, an exemplary recipe for a calibration solution having an excess of oxalate would be:

| | |
|---|---|
| potassium oxalate monohydrate | (0.75 mmol/L) |
| ferric ammonium sulfate dodecahydrate | (0.25 mmol/L) |
| sulfuric acid | (0.05 mol/L) | and an exemplary recipe for a calibration solution having an excess of iron(III) would be:

| | |
|---|---|
| potassium oxalate monohydrate | (1.50 mmol/L) |
| ferric ammonium sulfate dodecahydrate | (15.0 mmol/L) |
| sulfuric acid | (0.05 mol/L). |

In each case, the balance is distilled deionized water. Suitable recipes can be established from the above for other oxalate sources (e.g., oxalic acid, sodium oxalate), other iron(III) sources (e.g., ferric chloride, ferric sulfate) or other acidifying consituents (e.g., hydrochloric acid). Similarly, through no more than routine experimentation, other photochemical precursors of carbon dioxide such as uranyl oxalate, vanadium(V)iron(III) oxalate or cobalt oxalate can be used.

The present use of ferrioxalate contrasts with its use in actinometry. In that field, the ferrioxalate is provided in acidic solution at high concentration, generally with a molar concentration of ferrioxalate of 0.006 moles/liter up to 0.15 moles per liter. As indicated in the chapter by Hugh A. Taylor entitled "Analytical Methods And Techniques For Actinometry" in *Analytical Photochemical Analysis* (J. M. Fitzgerald, ed., 1971), such actinometers may employ potassium ferrioxalate which has been precipitated and recrystallized (and thus contains neither excess oxalate nor excess iron (III)). Solutions of the potassium ferrioxalate are exposed to light of the unknown intensity, and then the exposed solution is combined with a developer solution of o-phenanthroline monohydrate in water. Ferrous ions produced as a by-product of the ferrioxalate decomposition react quantitatively with the chromagen to form a chromophore, that can be quantitated. It should thus be appreciated that, in such reaction, oxalate must not be in excess (or else the reduction of iron(III) to iron(II) will not be quantitative) and no use is made of the carbon dioxide product of ferrioxalate decomposition.

By contrast, the present solutions should normally correspond to 0.1 to 5 mM ferrioxalate, yielding about 8 mm Hg pCO2 to about 600 mm Hg pCO2, respectively. With iron(III) at stoichiometric amounts or more, this corresponds to 0.3 to 15 mM oxalate. With oxalate in excess, this corresponds to 0.1 to 5 mM iron(III).

Especially for blood gas instrument calibration, preferred ranges are those yielding pCO2 values of 30 to 75. This corresponds generally to 0.2 to 0.5 mM iron-(III) if oxalate is in excess and 0.6 to 1.5 mM oxalate if iron is in excess. Precise proportions to achieve a particular pCO2 value can be determined through routine experiments.

Oxalate can exceed 15 mM concentration without yielding more than 5 mM ferrioxalate (and thus more than 600 mm Hg pCO2), provided that iron (III) concentration does not exceed 5 mM. In such cases oxalate may be present up to its solubility limits (see Example 12, below). Excessive iron (III) levels, such as over 200 mM, are not desirable because of the light absorption by the excess iron (III).

The present calibration solutions are preferably stored under conditions that do not promote decomposition. In the case of the preferred ferrioxalate solutions, this generally means storage at room temperature or below, and shielding from light, especially light of 500 nm wavelength or less (blue or near-ultraviolet light). Nevertheless, provided that proper pH is maintained, brief exposures to temperatures of up to 50 C. are not deleterious, and shielding in dark glass or plastic bottles is usually adequate.

In the present exposure device and step, an aliquot of the calibrator solution is exposed to light of sufficient wavelength and intensity to decompose the precursor essentially completely. For ferrioxalate, the present examples show that, in general, carbon dioxide formed reaches a plateau at which small variations of exposure level (variations in irradiation time less than 10 seconds) do not cause significant changes (more than 2%) in carbon dioxide partial pressure.

Thus, upon such exposure (typically with blue or near-ultraviolet light for ferrioxalate) a reproducible amount of carbon dioxide gas is generated (measured, for example, in millimoles per liter). So long as the temperature and pressure of the liquid is reproducible when that liquid is introduced into the instrument at the measuring electrodes (e.g., the Severinghaus carbon dioxide electrode), such reproducible carbon dioxide concentration will translate into a reproducible carbon dioxide partial pressure. Furthermore, if the instrument produces a reproducible temperature at the measuring electrode (e.g., 37 C.) and the barometric pressure is measured, any changes in pressure will have a direct and calculable effect upon the partial pressure of carbon dioxide that either can be compensated for, to calibrate the electrode to an "actual" partial pressure of carbon dioxide, or can be left uncompensated to cancel out the same effect on the sample. Thus, if the barometric pressure is slightly below standard conditions (one atmosphere pressure at sea level), the carbon dioxide partial pressure of the exposed calibrant will be measured at a value slight below what it would have been at standard conditions. That variation could either be compensated for electrically or could be left alone to adjust for the same difference in the carbon dioxide partial pressure of the sample, which would also have a slightly raised value at the slightly depressed barometric pressure compared to measurement of the same sample under standard conditions.

While the volume of the aliquot of sample that is exposed can be controlled somewhat accurately, it is not necessary for this volume to be precisely controlled. This is because it is the concentration of carbon dioxide produced (measured, e.g., in mmol/l) rather than the amount of carbon dioxide produced (measured, e.g., in mmol) that correlates with the measured partial pressure. It is only necessary that the exposed aliquot be large enough to flush the chamber near the measuring electrode of any residual sample or buffer, and yield the reproducible pCO2 value unaffected by the pCO2 of any liquid that preceded it.

The conveying of the exposed aliquot of calibration liquid to the vicinity of the measuring electrode can occur by any conventional pumping or drawing technique. There is no effect of light on the exposed aliquot. It is important, however, that the exposed aliquot be prevented from gas exchange with any other liquid or gas between the time of exposure and the time of measurement.

Figure 3:
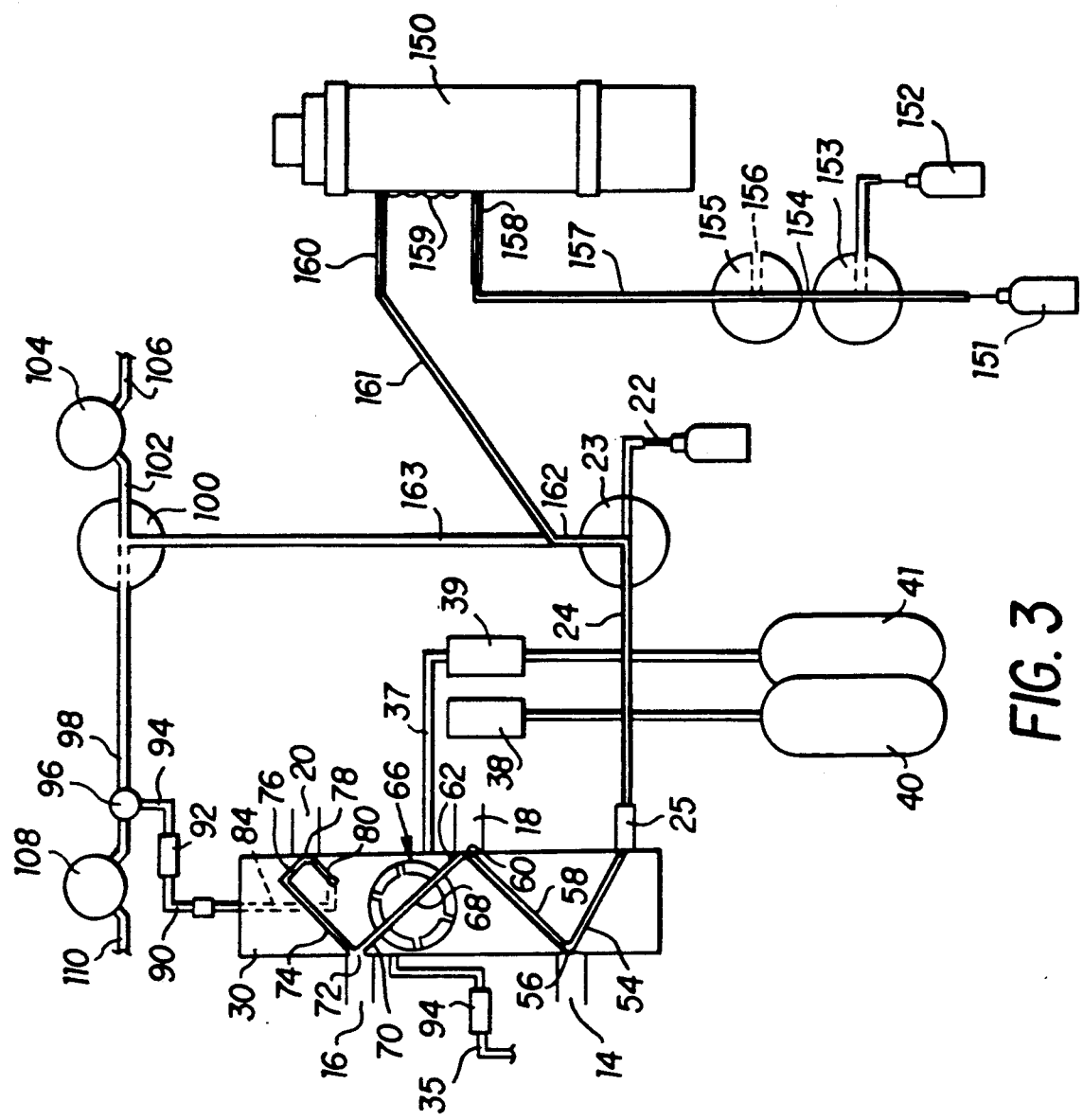
FIG. 3 is a schematic view of a test fixture used in conjunction with a Model 1312 Instrumentation Laboratory blood gas analyzer to demonstrate the present method.

The following Examples and the description of FIGS. 1 and 3 illustrate how the exposed aliquot can be brought into contact with the measuring electrode either along a sample pathway or along a calibrant pathway. The former is somewhat less preferred for ferrioxalate solutions in that, if the acidic exposed aliquot is brought into contract with a pH electrode (as would normally be the case in a sample pathway), the environment of the pH electrode becomes unusually acidic and must be flushed with liquids to bring it back to the desired range (e.g., to pH 7.0 to 7.6 for blood). As indicated at col. 7, lines 29–41 and col. 8, lines 22–31 of U.S. Pat. No. 4,361,539, a calibration pathway can be used instead that will bring the exposed calibrant into contact with the Clark oxygen electrode and with the Severinghaus carbon dioxide electrode, but not in contact with the pH electrode.

In some forms of the present invention, the same exposed aliquot is used to calibrate both for pCO2 and for pO2. For this purpose, the unexposed calibration liquid can be caused to So have a pO2 of known value, as by tonometry with room air. So long as the barometric pressure is known and temperature is controlled or known, the pO2 that results from such tonometry (liquid-gas equilibration) will be reproducible. The resultant pCO2 of the tonometered and unexposed liquid will also be reproducible, and essentially zero. Exposure of an aliquot of the liquid after such tonometry will cause the increase of the pCO2 value by a known amount, as described above. If the solution is one leading to carbon dioxide formation without oxygen consumption (e.g., a ferrioxalate solution with excess iron-(III)), then the exposed calibrant will retain the pO2 value established on tonometry. If the solution is of a composition leading to ferrioxalate decomposition accompanied by oxygen consumption, then the pO2 value will be depressed from the value established on tonometry by a reproducible amount. It should be appreciated that, if two calibrant solutions are used of the two different types (one having a stoichiometric excess of iron-(III), the other having a stoichiometric excess of oxa-late), then the liquids introduced into the measuring chambers after tonometry and exposure can be made to differ in a reproducible fashion in both pO2 and pCO2. This enables two liquids to be used to calibrate both electrodes at two values without any gas besides air being used.

Calibration of either or both electrodes at two values can be performed intermittently (e.g., at the start of each eight-hour shift and whenever control values show a need for recalibration) by exposing one calibrant, measuring and comparing to stored values, washing the electrodes, exposing the other calibrant, measuring and then comparing to other stored values. Such a two-point calibration differs from what is conventional in that each final calibrant is a liquid phase and has been generated by light exposure (or tonometry followed by light exposure) rather than by using humidified gas mixtures. Thus, the calibration medium (gases dissolved in an aqueous solution) more closely resembles the samples (e.g., whole blood), which are liquids. A one-point calibration can be performed either immediately before or immediately after measurement of values on each sample (conventionally the one-point calibration is performed before the sample measurement so that final values can be reported immediately after the measurement on the sample).

In addition to solutions such as the above-describe ferrioxalate solutions, the method and apparatus of the present invention can employ inorganic powders suspended in carboxylate-containing solution or inorganic colloids in such carboxylate-containing solutions, whereby the solid phase will catalyze the conversion in response to light of a dissolved carboxylate into carbon dioxide.

Alternatively, solutions of a carbonate or bicarbonate in defined amounts can be combined with a material that is photochemically converted into an acid, so as to change the carbonate or bicarbonate into carbon dioxide. Still alternatively, the material described as HCD (heterocoerdianthrone) in Brauer et al, Photochemistry And Photobiology, vol. 37, no. 5, pp. 587–91 (1983) can be used to generate oxygen in response to ultraviolet light (or to consume oxygen in response to visible light).

Referring now to FIG. 1, an apparatus is shown in schematic form, for calibrating a blood gas instrument. The flow cell 30 shown in FIG. 1 is described in detail in U.S. Pat. Nos. 4,443,407 and 4,361,539, which should be consulted for mechanical and other details of the arrangement of electrodes, inlets, outlets and temperature control devices. Two alternate sample inlets 22a and 22b are each connected to valve 23 for alternate connection to sample line 24. Sample line 24 is connected to flow cell 30 through sample preheater 25 (shown as preheater 130 in the Figures of U.S. Pat. Nos. 4,443,407 and 4,361,539).

Four electrodes are each connected to flow cell 30 by insertion in sleeves through heat blocks on either side of flow cell 30 as shown in FIGS. 3 and 10A of U.S. Pat. No. 4,361,539. The pO2 electrode 14 terminates at sensor port 56 in flow cell 30. The pH sensing electrode 16 terminates at sensor port 72 in flow cell 30. The pCO2 electrode 18 terminates at sensor port 60 in flow cell 30. The pH reference electrode 20 terminates at sensor port 78 in flow cell 30.

A flow control valve 66 is provided in flow cell 30, and is adjustable between three operative positions as is described in more detail in U.S. Pat. No. 4,361,539. One of the calibrating positions is illustrated in FIG. 15 of that patent and in present FIG. 1. Another of the calibrating positions is described at col 8, lines 23-31 of that patent. The analysis position is illustrated in FIGS. 10A and 11 of that patent and in present FIG. 3. In that analysis position, sample line 24 is connected to position sensor 88 by a pathway comprising first leg 54, second leg 58, third leg 62, transverse passage 68 through valve 66, fourth leg 70, fifth leg 74, sixth leg 76, seventh leg 80 and outlet passage 84. As described more fully in the prior patents, a blood sample is conveyed by the instrument in the analysis position past sensor ports 56, 60, 72 and 78, so that the sample can be measured by electrodes 14, 16, 18 and 20 in a fashion which is now conventional in the blood gas field. Position sensor 88 (illustrative of the several position sensors described at col. 7, lines 7-25, of U.S. Pat. No. 4,361,539) can be considered the top (downstream) end of the sample analysis region.

In the calibration position shown in FIG. 1, valve 66 has been turned so that transverse passage 68 communicates with neither third leg 62 nor fourth leg 70. Instead, a first buffer solution in line 35 is connected through buffer preheater 194 to a passage in valve 66 not shown in the present Figures (but indicated as 88b in U.S. Pat. No. 4,361,539). That passage connects line 35 to fourth leg 70 so that buffer can be drawn into fourth leg 70, fifth leg 74, sixth leg 76 and seventh leg 80 so as to be in contact with pH sensing electrode 16 at sensing port 72 and in contact with pH reference electrode 20 at sensing port 78 and to form an electrical connection therebetween. Measurement of the voltage difference between electrodes 16 and 20 is used to calibrate the pH measurement in a conventional fashion.

Also in the calibration position shown in FIG. 1, a calibrant line 37 is connected through a passage in valve 66 to second leg 62. Such connection within valve 66 is shown as passage 88a in U.S. Pat. No. 4,361,539. Whereas, in the prior art devices, the calibrant line is connected to a bubble chamber, in the present system, it is connected to an irradiation chamber as described more fully below.

To complete the conventional portion of the system of FIG. 1, outlet passage 84 is connected through position sensor 88, line 90, flush preheater 92 and line 94 to valve 96. In the analysis mode and calibration mode, valve 96 is positioned to connect line 94 through lines 98 and 102 to an aspirator pump 104, which draws either sample or calibrant into line 106 and then to waste. In this embodiment, a bypass valve 100 has been positioned between line 98 and line 102, has been connected via line 144 to a valve 143. Valve 143 has been positioned to connect calibrant in line 142 with leg 62 via line 37 and a passage through valve 66. A pump 198 is connected through valve 200 to sample preheater 25. Activation of pump 198 in the positioning of valves 143, 66 and 200 shown in FIG. 1 draws calibrant liquid from line 142 through line 37 into legs 62, 58 and 54. The outlet of pump 198 is to waste, which may be a separate waste container or may be the outlet to waste through sample tip 22 as shown in FIG. 1.

A unique aspect of the present invention relates to how calibrant is prepared for introduction into legs 62, 58 and 54 of flow cell 30 through calibrant line 37. Two reservoirs of calibration liquid 151 and 152 are each connected to a selector valve 153. Selector valve 153 can connect either reservoir to one inlet 154 of intake valve 155. Intake valve 155 can connect either selector valve 153 or a connection to room air via line 156 to an inlet line 157.

A tonometer device such as a device which passes the liquid past a gas-permeable membrane or which bubbles air through the liquid may be located along inlet line 157. Alternatively, such equilibration with room air may occur in containers 151 and 152. The pressure and temperature at the time of such equilibration should preferably be carefully controlled to have a consistent value or, if not so controlled, then should be carefully measured so as to be compensated for.

Inlet line 157 is connected through an uncovered glass tube inlet portion 158 of irradiation device 150 to the coil portion 159 of irradiation device 150. The coil portion 159 is connected at its opposite end to an outlet line 142 (which includes uncovered glass tube outlet portion 160 of irradiation device 150) to a branch point with line 144 near one inlet to valve 143.

To expose an aliquot of the calibration liquid in reservoir 151, valves 153 and 155 are positioned to connect reservoir 151 to line 157. Simultaneously, valves 100 and 143 are positioned to connect line 144 to line 102 and aspiration pump 104, but to disconnect line 144 from line 37. Operation of aspiration pump 104 in this position will draw calibration liquid from reservoir 151 into coil portion 159 of irradiation device 150. Upon activation of the light source in irradiation device 150, as described below, essentially complete photochemical reaction will occur on the aliquot of calibration liquid which is then in coil portion 159.

Depending upon the relative volumes of liquid in coil portion 159 and drawn therefrom by aspiration pump 104, the aliquot of calibration liquid in line 142 may either be exposed or unexposed. In one preferred case, the volume of coil portion 159 is larger than the amount pumped each time so that line 142 is always filled with exposed calibration liquid. In another case, as is described below in connection with FIG. 3, air is admitted through line 156 and valve 155 between each aliquot of calibration liquid so that each aliquot fills coil portion 159 between exposed glass tube portions 158 and 160. In such case, the entire aliquot becomes exposed except for a small leading edge fraction which is in tube portion 160 during exposure and a small trailing edge portion which is in tube portion 158 and line 157 during exposure.

Upon completion of irradiation, valves 100, 143 and 66 are adjusted to connect line 142 through line 37 to legs 62, 58 and 54 in the serpentine flow path through flow cell 30. Pump 198 can then draw calibration liquid from coil portion 159 through lines 142 and 37 into the serpentine flow path in contact with pCO2 electrode at sensor port 60 and in contact with pO2 electrode at sensor port 56.

If the aliquot had occupied only the coil portion 159 from tube portion 158 to tube portion 160 during exposure, then liquid position sensors (not shown) can be used to ensure that the aliquot of calibration liquid which had been in coil portion 159 (and thus has undergone the photochemical reaction) fills the flow path throughout third leg 62, second leg 58 and first leg 54. Any aliquot of calibration liquid that had been in tube portion 160 during exposure should be drawn into or past preheater 25 (and preferably past pump 198). Any aliquot of calibration liquid that had been in line 157 or tube portion 158 during exposure should remain in line 37 at the time that calibration measurements are being taken by electrodes 14 and 18.

Figure 2:
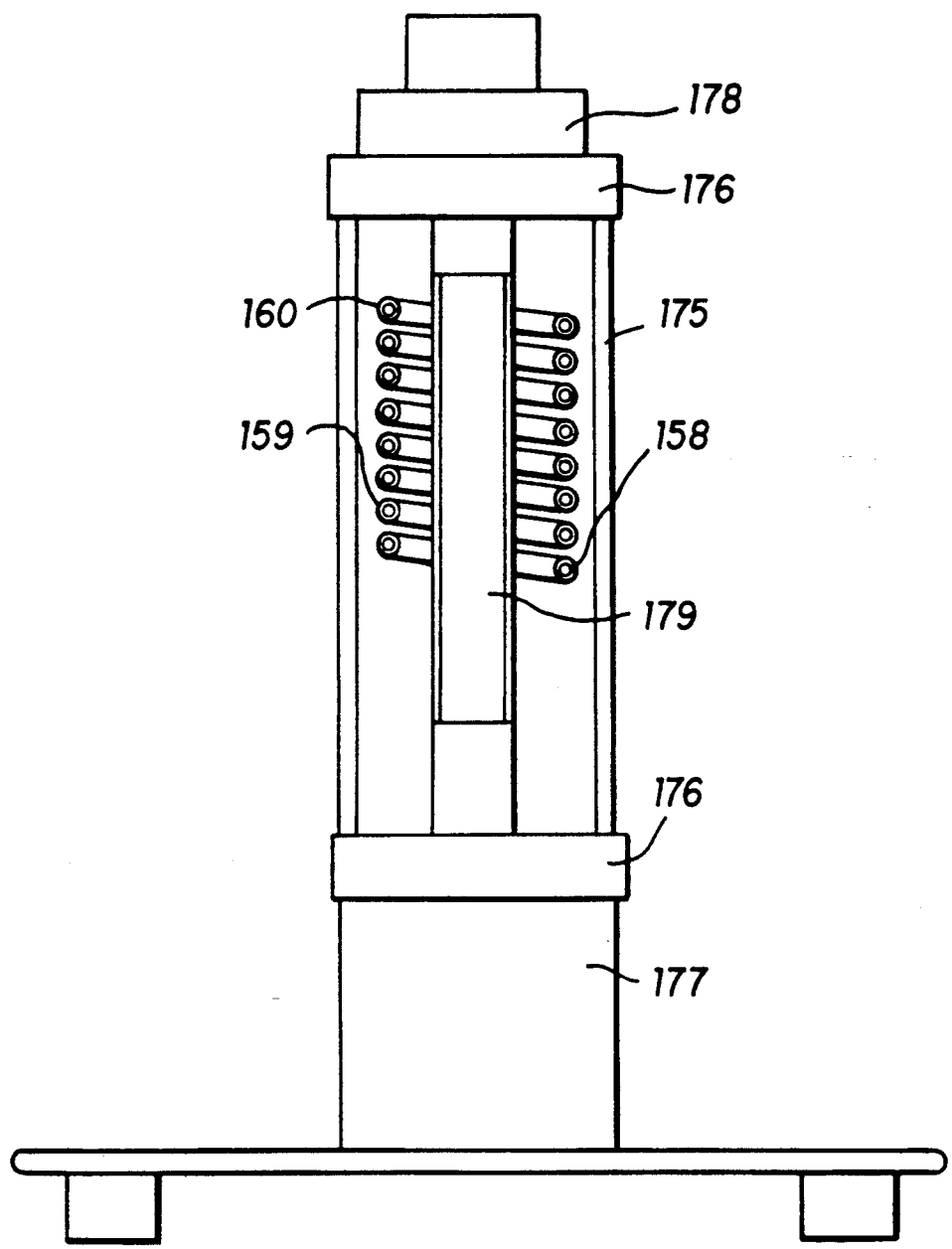
FIG. 2 is an elevational view, partly in section, of the exposure device of the apparatus of FIG. 1.

As illustrated in FIG. 2, the structure of irradiation device 150 includes a heat-resistant glass (e.g. PYREX)

tube 159 wound helically around a cylindrically lamp 179. The irradiation device also includes an aluminum housing 175, a base section 177 with a fan and sleeves 176 above and below the cylindrical lamp 179 to position the lamp 179 centrally within aluminum housing 175. A vented cap portion 178 has vents for cooling air to flow out and a recess for receiving the top of lamp 179. As shown in FIG. 1, the lower end 158 and upper end 160 of tube portion 159 extend out through holes in aluminum housing 175.

Referring now to FIG. 3, a system is shown by which the present invention has been demonstrated in the Examples, but which system is less preferred to that of FIG. 1 for practise of the present invention. The flow cell 30 in FIG. 3 is identical to flow cell 30 of FIG. 1 except that valve 66 is shown in the analysis position (which is also used for flushing the sample pathway). In this position, aspiration pump 104 can apply a vacuum to outlet line 84 through lines 90, 94, 98 and 102, with valves 96 and 100 being appropriately positioned. Such vacuum at outline line 84 can draw sample from sample valve 23 through sample inlet line 24 and sample preheater 25 into the serpentine flow path consisting of first leg 54, second leg 58, third leg 62, transverse passage 68 in valve 66, fourth leg 70, fifth leg 74, sixth leg 76 and seventh leg 80, which is connected to outlet line 84.

With sample filling the serpentine flow path, it is in contact with pO2 electrode 14 at sensor port 56, with pCO2 electrode 18 at sensor port 60, with pH sensing electrode 16 atsensor port 72 and with pH reference electrode 20 at sensor port 78. Measurements can be taken on the sample in the serpentine flow path in a conventional fashion.

By changes at valves 96 and 43, sample can be flushed from the serpentine flow path with valve 66 remaining in the position shown in FIG. 3. Flush pump 108 can then draw flush liquid (e.g., an aqueous solution containing a silicone liquid and a surfactant) from line 110 and through valve 96, line 94, flush preheater 92, and line 90 into outlet passage 84. Flush liquid is then pumped through legs 80, 76, 74 and 70, transverse passage 68 and legs 62, 58 and 54 so as to push sample out of the serpentine flow path. From leg 54, sample and then flush liquid flows through sample preheater 25, sample line 24, valve 23 and line 22 to waste.

FIG. 3 represents a conventional blood gas instrument to which irradiation device 150 has been connected for purposes of demonstrating the present invention. Therefore calibration line 37 is connected to a first bubble chamber 39 (designated 152 in U.S. Pat. No. 4,361,539) which is fed by a first gas mixture in a first gas tank 41. A second calibration line (not shown, but referred to as 164 in U.S. Pat. No. 4,361,539) is connected from an inlet to valve 66 to a second bubble chamber 38 (designated 154 in that patent) which is fed by a second gas mixture in a second gas tank 40. The structure of such bubble chambers are illustrated in FIG. 3 of U.S. Pat. No. 4,361,539. For purposes of demonstrating the present invention, the instrument was calibrated prior to each measurement of irradiated calibrant by gas from first bubble chamber 39, and was also periodically calibrated by a two-point calibration, using both first and second bubble chambers 38 and 39. As described in U.S. Pat. No. 4,361,539, valve 66 is turned to one position to connect bubble chamber 38 to leg 62 and to another position to connect bubble chamber 39 to leg 62.

In the arrangement shown in FIG. 3, the sample valve 23 has been used to connect irradiation chamber 150 to the serpentine flow path through flow cell 30. It will be appreciated that a sample valve is already present in the Instrumentation Laboratory Model 1312 Blood Gas Instruments, but is used there to connect two different sample inlets to the sample preheater (typically a regular inlet for drawing 120 microliter samples, and a second inlet for drawing 65 microliter samples). In the system shown in FIG. 3, sample valve 23 can connect sample inlet line 24 either to line 22 (which goes to waste) or via line 162 to line 161. Line 163 also connects line 162 to valve 100 between line 98 and 102.

As with the system shown in FIG. 1, irradiation chamber 150 is connected in FIG. 3 so as to draw calibration liquid from either reservoir 151 or reservoir 152 through selector valve 153, line 154, intake valve 155, line 157 and exposed glass tube portion 158 into coil portion 159 of irradiation device 150. Vacuum was applied by aspiration pump 104 through line 102, bypass valve 100, line 163, line 161 and outlet section 160 on coil portion 159. Aspiration pump 104 was operated so as to ensure that coil portion 159 was filled from portion 158 to portion 160 with an aliquot of the desired calibration liquid. Once coil portion 159 was filled with liquid, valve 155 was turned to connect line 157 through line 156 to room air. By having line 157 connected to line 154 only when coil portion 159 was being filled with calibration liquid, air was introduced both ahead of and behind each aliquot of calibration liquid.

After exposure of the aliquot of calibration liquid in device 150, valves 156, 23 and 100 were turned (and valve 68 rotated to the position shown in FIG. 3 if not already there) so that aspiration pump 104 could apply vacuum to outlet portion 84 of the serpentine flow path through flow cell 30. Exposed calibration liquid in coil portion 159 was drawn into flow cell 30 through lines 161 and 162, valve 23, sample inlet line 24 and sample preheater 25.

Aspiration pump 104 was operated in this position sufficiently long to ensure that the aliquot of calibration liquid which had been exposed in coil portion 159 occupied at least the first three legs 54, 58 and 62 of the serpentine flow path. Normally, that aliquot was sufficiently large to also fill transverse passage 68 through valve 66 and legs 70, 74, 76 and 80 and part or all of outlet passage 84 up to sensor 88. To obtain a valid measurement on fully exposed calibration liquid, any aliquots which had been in exposed tube portion 160 or line 161 during exposure should, during measurement, be in or above transverse passage 68 (and normally such aliquots were in outlet passage 84 or beyond). Any aliquot of treating liquid which had been in line 157 or tube portion 158 during the lastest exposure should be to the right of sample preheater 25 (i.e., in line 24, 162 or 161) at the time of analysis.

As described above, flush pump 108 can be connected by valve 96 to the top end of the serpentine flow path (i.e., at outlet passage 84) and probe 22 could be connected to waste to the bottom end of the serpentine flow path. After flushing calibrant out of the flow path, a sample could be introduced into sample probe 22.

If line 37 in FIG. 3 were not used for connection to a bubble chamber, it would be possible to leave irradiation chamber 150 connected via valve 23 to sample inlet line 24. Line 37 would then be connected to a new valve along line 163. When irradiation chamber 150 is being filled with calibration liquid, that new valve would connect aspiration pump 104 through valve 100 and lines 163 and 161 to tube portion 160 as shown in FIG. 3. After completion of the photochemical reaction, that new valve and valve 100 would be rotated so as to connect line 37 through the new valve, the top portion of line 163 and valve 100 to aspiration pump 104. With valve 23 then connecting lines 161 and 162 to sample inlet line 24 and valve 66 turned to connect third leg 62 of the serpentine flow path to line 37, operation of the aspiration pump 104 would then apply vacuum to line 37 and draw calibrant from coil portion 159 through lines 161, 162 and 24 into the bottom portion of the serpentine flowpath (i.e., legs 54, 58 and 62). By so drawing calibrant by application of vacuum to line 37, valve 66 is positioned to also connect buffer line 35 to leg 70. Either before or after the calibrant is drawn into the bottom portion of the serpentine flow path, buffer can be drawn from line 35 (through preheater 94) into the top portion of the serpentine flow path consisting of legs 70, 74, 76 and 80 by the application of vacuum to outlet passage 84. Depending upon which electrodes require the most time to stabilize, valve 100 can be turned to have aspiration pump 104 apply vacuum first to outlet passage 84 and then to line 34 or vice versa.

Figure 4:
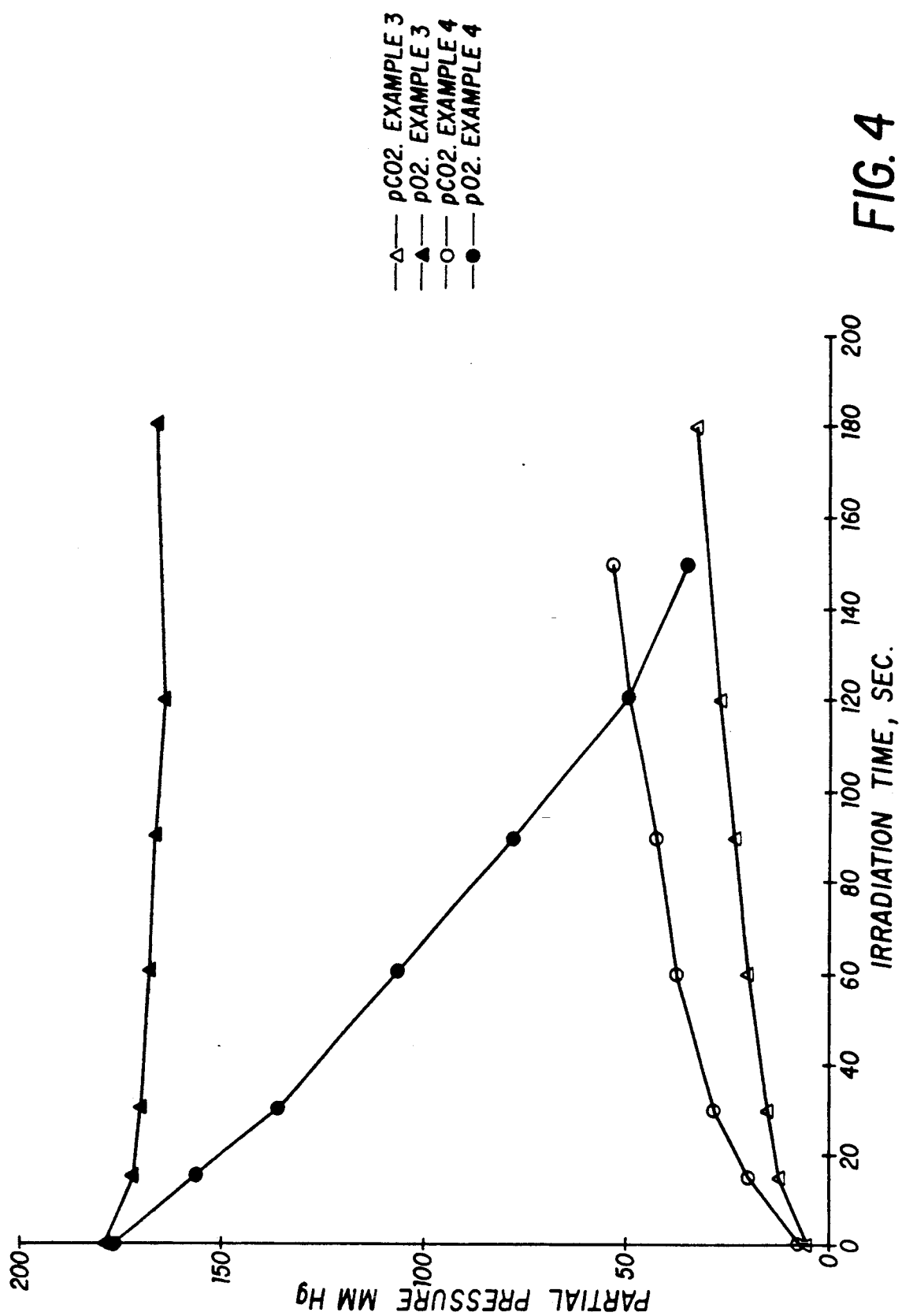
FIG. 4 is a graphic representation of the partial pressure in millimeters of mercury (torr) of oxygen and of carbon dioxide measured on a blood gas instrument with two calibration liquids according to embodiments of the present invention, after varable amounts of time of light exposure.

FIG. 4 displays data obtained using the system shown in FIG. 3. The blood gas instrument was calibrated with liquid from bubble chambers as shown. Measurements of the exposed calibrant (treated as sample, but ignoring the pH measurements which would have all been off-scale on the acidic side) as a function of calibration liquid concentration and exposure levels are shown. The triangles all represent values with a calibration liquid of the composition shown in Example 3. The circles all represent values with a calibration liquid of the composition shown in Example 4. The values for $pCO_2$ can be seen to reach a final level for each liquid at exposure times of 120 seconds or more. For the calibration liquid of Example 3, the values of $pO_2$ are essentially unaffected by exposure level. As indicated above, the oxalate to iron(III) ratio of this composition is sufficiently low that photochemical reaction proceeds by mechanisms that generate carbon dioxide without consuming oxygen (instead, some of the excess iron(III) is reduced). The values for $pO_2$ of the calibration liquid of Example 4 can be seen to fall with increased exposure level, and to begin to plateau at 150 seconds or more of exposure. Thus, if these two liquids are used for calibration after tonometry with room air and then exposure in irradiation device 150, they will provide calibration levels (in mm Hg) of 33 and 53, respectively, for $pCO_2$ and of 165 and 35 or less, respectively, for $pO_2$, so long as the exposure times are sufficient for these values to reach the plateaus.

EXAMPLES

Example 1

An aqueous solution containing 50 mM sulfuric acid, 0.75 mM potassium oxalate monohydrate and 0.25 mM ferric ammonium sulfate dodecahydrate was prepared and equilibrated with room air in the absence of light. Aliquots of this solution, each 300 microliters, were placed in a commercially available SUPRASIL quartz optical cuvette (Catalog Number 14-385-927B from Fisher Scientific Company) having an optical path length of 1.0 cm. The cuvette was sealed with a silicone rubber cap to limit the headspace above the solution to no more than 80 microliters. Different aliquots were irradiated for different lengths of time by placing the cuvette directly in front of a Pyrex glass-filtered xenon flash lamp (Model FX-193U lamp with a Model FY-714 trigger module operated by a Model PS302 power supply, all from EG&G Electro-optics; the power supply was externally triggered by a Model 175 universal programmer from EG&G PARC.) The lamp was operated at 275 Herz with an average power of 16 Watts. Immediately after irradiation, each aliquot was run on an unmodified Instrumentation Laboratory Model 1312 blood gas instrument, as a sample drawn into the main sample port.

Values for $pCO_2$ and $pO_2$ given by the instrument for two replications of these aliquots were recorded and are tabulated in Table I.

TABLE I

| Irradiation Time in seconds | Average $pCO_2$ in mm Hg | Average $pO_2$ in mm Hg |
|---|---|---|
| 0 | 7.5 | 197 |
| 30 | 17.2 | 85 |
| 60 | 21.6 | 36 |
| 90 | 27.0 | −2 |
| 120 | 31.1 | −2 |
| 150 | 32.6 | −2 |
| 180 | 34.0 | −1 |
| 240 | 34.9 | 6 |

An evaluation of this data shows the $pCO_2$ values reaching a plateau within 120 seconds and the $pO_2$ values declining to essentially 0 within 90 seconds. The small oxygen value after 180 seconds is believed to be caused by contamination.

Example 2

An aqueous solution was prepared and equilibrated as in Example 1, but now containing 50 mM sulfuric acid, 1.50 mM potassium oxalate monohydrate and 15.0 mM ferric ammonium sulfate dodecahydrate. Aliquots of 300 microliter volume were irradiated and immediately run on the Model 1312 blood gas instrument as in Example 1. Results of two replications are tabulated in Table 2.

TABLE 2

| Irradiation Time in seconds | Average $pCO_2$ in mm Hg | Average $pO_2$ in mm Hg |
|---|---|---|
| 0 | 7.6 | 195 |
| 30 | 35.2 | 191 |
| 60 | 51.9 | 188 |
| 90 | 65.4 | 185 |
| 120 | 71.8 | 185 |
| 150 | 75.4 | 181 |
| 180 | 76.6 | 180 |
| 240 | 75.3 | 179 |

An evaluation of this data shows the $pCO_2$ values reaching a plateau within 150 seconds and the $pO_2$ values declining only about 8%.

Example 3

An aqueous solution containing 50 mM sulfuric acid, 0.68 mM potassium oxalate monohydrate and 13.5 mM ferric ammonium sulfate dodecahydrate was prepared and equilibrated with room air in the absence of light. The amber polyethylene container in which the solution was stored was connected to a modified Model 1312 blood gas instrument in the manner shown in FIG. 3. Using a personal computer to automatically regulate the various pumps shown in FIG. 3 and the circuits controlling the valves shown in FIG. 3, the aqueous solution was introduced into the irradiation chamber shown in FIG. 2. The programming of the personal computer caused irradiation device 150 to operate at an average power of 8 Watts for a variable length of time. Upon completion of the exposure, the aliquot of liquid then in irradiation device 150 was brought into the blood gas instrument as shown in FIG. 3 and run as a sample. Details of the fluidic cycle are described above in connection with FIG. 3. In particular, each 300 microliter aliquot of liquid was drawn from the amber polyethylene container into an exposure position in which its leading edge was in exposed tube portion 160. Then, after exposure, and with valve 155 turned to admit air through line 156 behind the aliquot, that leading edge was drawn through lines 161 and 24 into the serpentine path in the blood gas instrument and past the leg 80 of that path until it was sensed by position sensor 88.

Values of pCO2 and pO2 obtained for three replications of the various irradiation times are tabulated in Table III and displayed as triangles in FIG. 4.

TABLE III

| Irradiation Time in seconds | Average pCO2 in mm Hg | Average pO2 in mm Hg |
| --- | --- | --- |
| 0 | 5.0 | 179 |
| 15 | 12.4 | 172 |
| 30 | 15.0 | 170 |
| 60 | 19.8 | 168 |
| 90 | 23.5 | 167 |
| 120 | 26.9 | 165 |
| 180 | 33.0 | 167 |

An evaluation of this data shows the pCO2 values approaching the plateau within 180 seconds and the pO2 values not declining significantly over that period. A higher power in irradiation device 150 would be expected to enable the plateau value of pCO2 to be reached more quickly, e.g., in sixty seconds or less.

Example 4

An aqueous solution was prepared and equilibrated as in Example 3, but now containing 50 mM sulfuric acid, 1.35 mM potassium oxalate monohydrate and 1.35 mM ferric ammonium sulfate dodecahydrate. Aliquots of this solution were irradiated and run in the Model 1312 blood gas instrument as described in Example 3. Results are tabulated in Table IV and shown as circles in FIG. 4.

TABLE IV

| Irradiation Time in seconds | Averaqe pCO2 in mm Hg | Average pO2 in mm Hg |
| --- | --- | --- |
| 0 | 7.0 | 176 |
| 15 | 19.8 | 156 |
| 30 | 27.9 | 136 |
| 60 | 37.1 | 106 |
| 90 | 42.4 | 78 |
| 120 | 49.2 | 50 |
| 150 | 53.5 | 35 |
| 180 | 55.8 | 26 |
| 210 | 55.2 | 27 |

An evaluation of this data shows the pCO2 values approaching the plateau within 180 seconds and the pO2 declining to a plateau within 180 seconds. Again, an increase in power applied at irradiation device 150 is expected to enable these plateau values to be obtained more quickly.

Examples 5-13

The procedures of Example 1 were followed for compositions having varying proportions of oxalate (as mM potassium oxalate) and iron(III) (as mM ferric ammonium sulfate) as indicated in Table V, below. Sulfuric acid was used at 500 mM in Examples 5 and 6, and at 50 mM in the other Examples. The plateau level of pCO2 and and % reduction in pO2 observed were as indicated in Table V. The results of Examples 1-4 are also summarized in Table V.

TABLE V

| Example | Fe(III) mM | Oxalate mM | Ratio | pCO2 | % pO2 red |
| --- | --- | --- | --- | --- | --- |
| 1 | 0.25 | 0.75 | 1:3 | 35 | 100 |
| 2 | 15.0 | 1.5 | 10:1 | 75 | 8 |
| 3 | 13.5 | 0.68 | 20:1 | 33 | 7 |
| 4 | 1.35 | 1.35 | 1:1 | 55 | 85 |
| 5 | 15.0 | 0.75 | 20:1 | 37 | 10 |
| 6 | 27 | 1.35 | 20:1 | 46 | 7 |
| 7 | 0.25 | 5.0 | 1:20 | 35 | 100 |
| 8 | 0.25 | 50 | 1:200 | 39 | 95 |
| 9 | 0.25 | 100 | 1:400 | 39 | 95 |
| 10 | 0.25 | 500 | 1:2000 | 39 | 100 |
| 11 | 0.25 | 1000 | 1:4000 | 38 | 100 |
| 12 | 0.25 | 1800 | 1:7200 | 35 | 100 |
| 13 | 0.25 | 250 | 1:1000 | 40 | 100 |
| 14 | 32.5 | 0.65 | 50:1 | 34 | 4 |
| 15 | 65 | 0.65 | 100:1 | 35 | 4 |

These results demonstrate the broad suitable ranges, 100:1 to 1:7200, and the preferred ranges of 2:1 to 1:7200 and 1:1 to 1:2000 for formulations that deplete oxygen and of 5:1 to 100:1 and 10:1 to 50:1 for formulations that do not deplete oxygen.

General Comments

In each of the above examples and in much of the description that precedes them, the actual measurement of pCO2 and of pO2 was electrochemical (with a Clark oxygen electrode and a Severinghaus carbon dioxide electrode). The present method and apparatus are not, however, so limited in that other modes of measurement, such as optical measurement of pO2 and of pCO2, can be employed. The irradiated calibration solution would be expected to perform satisfactorily with such non-electrode measuring elements.

The step of comparing the value measured by the measuring element on the liquid sample to the value measured by the measuring element on the exposed calibration liquid can be either a one-point calibration, a two-point calibration or another mode of comparison. For example, the electronic circuitry can take the signal from the measurement of the exposed solution of Example 3 as the values for 33 mm Hg pCO2 and for 167 mm Hg pO2 and the values for the signal from the measurement of the exposed solution of Example 4 as the values for 55 mm Hg pCO2 and for 26 mm Hg pO2. From these two known values, functional relationships of signal to partial pressure can be established (e.g., linear relationships); and each signal generated when a measuring element measures a liquid sample can be converted to a partial pressure according to the respective functional relationship. Furthermore, one of the two sets of calibration values (e.g., the values for 55 mm Hg pCO2 and for 26 mm Hg pO2) can be stored over many sample measurements while the other set (e.g., the values for 33 mm Hg pCO2 and for 167 mm Hg pO2) can be reset by measuring an exposed aliquot of one calibration liquid prior to each sample measurement. In such cases, the pO2 of the calibration liquid whose values are stored is preferably 0 mm Hg.

What is claimed is:

1. A method for the measurement of the partial pressure of a gas in a liquid sample which comprises the steps:
    a) providing a calibration liquid having a defined concentration of a dissolved precursor of a gas, the liquid having a composition such that, upon exposure to light, the dissolved precursor reacts to form the gas;
    b) exposing an aliquot of the calibration liquid in an exposing means to light of sufficient wavelength, intensity and duration to convert the precursor substantially completely to the gas;
    c) conveying the exposed aliquot with the converted precursor to a measuring chamber for contact with a measuring element for the partial pressure of the gas;
    d) making a measurement with the measuring element on the exposed aliquot with the converted precursor;
    e) conveying the exposed aliquot with the converted precursor away from the measuring element and conveying a liquid sample having an analyte value of the partial pressure of the gas into the measuring chamber in contact with the measuring element;
    f) making a measurement with the measuring element on the liquid sample; and
    g) comparing the measurement made with the measuring element on the liquid sample to the measurement made with the measuring element on the exposed aliquot of calibration liquid.

2. The method of claim 1 wherein the measuring element is a carbon dioxide electrode.

3. The method of claim 2 wherein the calibration liquid contains a dissolved carbon dioxide precursor which is a photoreactive complex anion of a metal and an carboxlic acid.

4. The method of claim 3 wherein the dissolved carbon dioxide precursor is ferrioxlate anion.

5. The method of claim 4 further comprising equilibrating the aliquot of calibration liquid with air prior to exposing the aliquot in the exposing means.

6. The method of claim 4 wherein the calibration liquid has a pH of 0 to 5, contains at least 0.3 millimoles per liter of oxalate, contains 0.1 to 200 millimoles per liter of iron(III) and has a molar ratio of iron(III) to oxalate of 100:1 to 1:7200, provided that when the iron(III) concentration is greater than 5 millimoles per liter, then the oxalate concentration is not greater than 15 millimoles per liter.

7. The method of claim 6 wherein the calibration liquid has a pH of 0 to 2.

8. The method of claim 7 wherein the calibration liquid has a molar ratio of iron(III) to oxalate of 2:1 to 1:7200.

9. The method of claim 7 wherein the calibration liquid has a molar ratio of iron(III) to oxalate of 5:1 to 100:1.

10. The method of claim 2 wherein the dissolved carbon dioxide precursor is uranyloxalate.

11. The method of claim 1 further comprising equilibrating the aliquot of calibration liquid with air prior to exposing the aliquot in the exposing means.

12. The method of claim 1 wherein the sample liquid is conveyed into the measuring chamber along a first pathway that also brings the sample into contact with a pH electrode and wherein the exposed aliquot of calibration liquid is conveyed into the measuring chamber along a second pathway that does not bring the exposed aliquot into contact with the pH electrode.

13. An apparatus for measuring the partial pressure of a gas in a liquid sample which comprises:
    a) exposure means for exposing an aliquot of a calibration liquid to light;
    b) a measuring chamber;
    c) first conveying means for conveying an exposed aliquot of calibration liquid from the exposure means to the measuring chamber;
    d) a measuring means in operative contact with the measuring chamber;
    e) second conveying means for conveying a liquid sample into the measuring chamber; and
    f) comparator means for comparing the measurement made by the measuring element on the liquid sample with the measurement made by the measuring element on the exposed aliquot of calibration liquid.

14. The apparatus of claim 13 wherein the second conveying means is constructed so as to convey sample along a first pathway that brings liquid sample into the measuring chamber, wherein said measuring means comprises a pCO2 electrode and a pH electrode, and wherein the first conveying means is constructed so as to convey exposed calibration liquid into the measuring chamber without bringing exposed calibration liquid into contact with the pH electrode.

15. The apparatus of claim 13 further comprising tonometry means for equilibrating the aliquot of calibration liquid with air prior to exposing the aliquot of calibration liquid to light in the exposure means.

16. The apparatus of claim 13 further comprising two reservoirs of calibration liquid, and wherein the tonometry means, exposure means and first conveying means are operative to equilibrate, expose and convey into the measuring chamber either an aliquot of calibration liquid in the first reservoir or an aliquot of calibration liquid in the second reservoir.

17. A method for the measurement of the partial pressure of oxygen and carbon dioxide in a liquid sample which comprises the steps:
    a) providing first and second calibration liquids comprising aqueous ferroxalate solutions:
        1) the first calibration liquid having a pH of 0 to 2, an oxalate concentration of 0.6 to 1.5 millimoles per liter, a molar ratio of iron(III) to oxalate of 5:1 to 100:1 and an iron concentration of 3 to 150 millimoles per liter; and
        2) the second calibration liquid having a pH of 0 to 2, an iron concentration of 0.1 to 0.5 millimoles per liter, a molar ratio of iron (III) to oxalate of 1:1 to 1:7200 and an oxalate concentration of at least 0.3 millimoles per liter;
    b1) exposing an aliquot of the first calibration liquid to light of sufficient wavelength, intensity and duration to convert the oxalate substantially completely to carbon dioxide without affecting the oxygen partial pressure;
    c1) conveying the exposed aliquot of first calibration liquid to a measuring chamber for contact with measuring elements for partial pressure of oxygen and of carbon dioxide;

d1) making a measurement with the measuring elements on the exposed aliquot of first calibration liquid;

b2) exposing an aliquot of the second calibration liquid to light of sufficient wavelength, intensity and duration to convert the ferrioxalate substantially completely to carbon dioxide with a concombitant reduction of oxygen partial pressure;

c2) conveying the exposed aliquot of second calibration liquid to the measuring chamber for contact with the measuring elements for the partial pressures of oxygen and carbon dioxide;

d2) making measurements with the measuring elements on the exposed aliquot of second calibration liquid;

e) conveying a liquid sample having analyte values for the partial pressures of oxygen and carbon dioxide into the measuring chamber in contact with the measuring elements for the partial pressures of oxygen and carbon dioxide;

f) making measurements with the measuring elements on the liquid sample; and g1) comparing the measurements made of oxygen partial pressure with the measuring element therefore on the liquid sample with the measurements made by that measuring element on the aliquots of first and second calibration liquids, and g2) comparing the measurements made of carbon dioxide partial pressure with the measuring element therefore on the liquid sample with the measurements made by that measuring element on the aliquots of first and second calibration liquids.

18. The method of claim 17 wherein the measuring element for oxygen partial pressure is an electrode and the measuring element for carbon dioxide partial pressure is an electrode.

19. The method of claim 17 wherein the composition of the second calibration liquid is such that the partial pressure of oxygen is zero in the exposed aliquot of second calibration liquid.

20. The method of claim 17 wherein a plurality of liquid samples are subjected to the conveying step (e), making a measurement step (f) and comparing steps (g) (1) and (g) (2), and wherein the first calibration liquid is subjected to the exposing step (b) (1), conveying step (c) (1) and making a measurement step (d) (1) once for the plurality of liquid samples, the comparing steps (g) (1) and (g) (2) for each of the plurality of liquid samples making use of the same values of oxygen and carbon dioxide partial pressure measured in a common measuring step (d) (1).

21. The method of claim 20 wherein a plurality of aliquots of second calibration liquid are subjected to the exposing step (b) (2), conveying step (c) (2) and making a measurement step (d) (2), the comparing steps (g) (1) and (g) (2) for each of the plurality of liquid samples making use of distinct values of oxygen and carbon dioxide partial pressure measured in distinct measuring steps (d) (2).

* * * * *

UNITED STATES PATENT AND TRADEMARK OFFICE
CERTIFICATE OF CORRECTION

PATENT NO. : 5,061,631

DATED : October 29, 1991

INVENTOR(S) : Gary S. Calabrese

It is certified that error appears in the above-identified patent and that said Letters Patent is hereby corrected as shown below:

On the title page, item (75) should read --

Inventor: Gary S. Calabrese, North Andover, Mass. and Claudio Calzi, Milan, Italy
    ---.

Column 17, line 40, "an carboxlic" should be ---a carboxylic---.

Column 17, line 42, "ferrioxlate" should be ---ferrioxalate---.

Signed and Sealed this

Seventeenth Day of August, 1993

Attest:

BRUCE LEHMAN

Attesting Officer     Commissioner of Patents and Trademarks